United States Patent [19]

Kesling

[11] Patent Number: 4,921,423
[45] Date of Patent: May 1, 1990

[54] ORTHODONTIC LIGATURE GUN

[75] Inventor: Peter C. Kesling, LaPorte, Ind.

[73] Assignee: TP Orthodontics, Inc., Westville, Ind.

[21] Appl. No.: 317,220

[22] Filed: Feb. 28, 1989

[51] Int. Cl.$^5$ ............................................. A61C 3/00
[52] U.S. Cl. ....................................... 433/3; 606/140
[58] Field of Search ............... 433/3, 4; 128/303 A; 81/302, 303, 304, 305; 29/229

[56] References Cited

U.S. PATENT DOCUMENTS

| | | | |
|---|---|---|---|
| D. 270,758 | 9/1983 | Clarke et al. | D24/10 |
| 2,447,474 | 8/1948 | Hammond | 81/304 |
| 3,518,993 | 7/1970 | Blake | 81/303 |
| 4,001,940 | 1/1977 | Cusato | 433/3 |
| 4,040,187 | 8/1977 | Cardena | 433/3 |
| 4,106,374 | 8/1978 | Dragan | 81/302 |
| 4,127,940 | 12/1978 | Shilliday | 433/3 |
| 4,217,686 | 8/1980 | Dragan | 29/413 |
| 4,277,236 | 7/1981 | Kurz | 433/3 |
| 4,310,305 | 1/1982 | Frajdenrajch | 433/4 |
| 4,385,890 | 5/1983 | Klein | 433/4 |
| 4,472,137 | 9/1984 | Barone | 433/3 |
| 4,512,739 | 4/1985 | Kaniadakis | 433/3 |
| 4,668,186 | 5/1987 | Bally et al. | 433/3 |
| 4,768,950 | 9/1988 | Armstrong et al. | 433/3 |

FOREIGN PATENT DOCUMENTS 140769  4/1951  Australia .................... 128/303 A

OTHER PUBLICATIONS

TP Catalog 908, 1987, p. 113.
DCA Sales Bulletin, 1988, p. 4.

*Primary Examiner*—Cary E. Stone
*Attorney, Agent, or Firm*—Lloyd L. Zickert

[57] ABSTRACT

Device for applying elastic ligatures to an orthodontic bracket, which includes jaw elements spreadable for stretching an elastic ligature and for dispensing the ligature directly onto an orthodontic bracket in an orthodontic system so as to attach an archwire to a bracket. The device may be in the form of a gun which can be used first to load a ligature from a dispenser and then to unload the ligature around and onto a bracket.

18 Claims, 4 Drawing Sheets

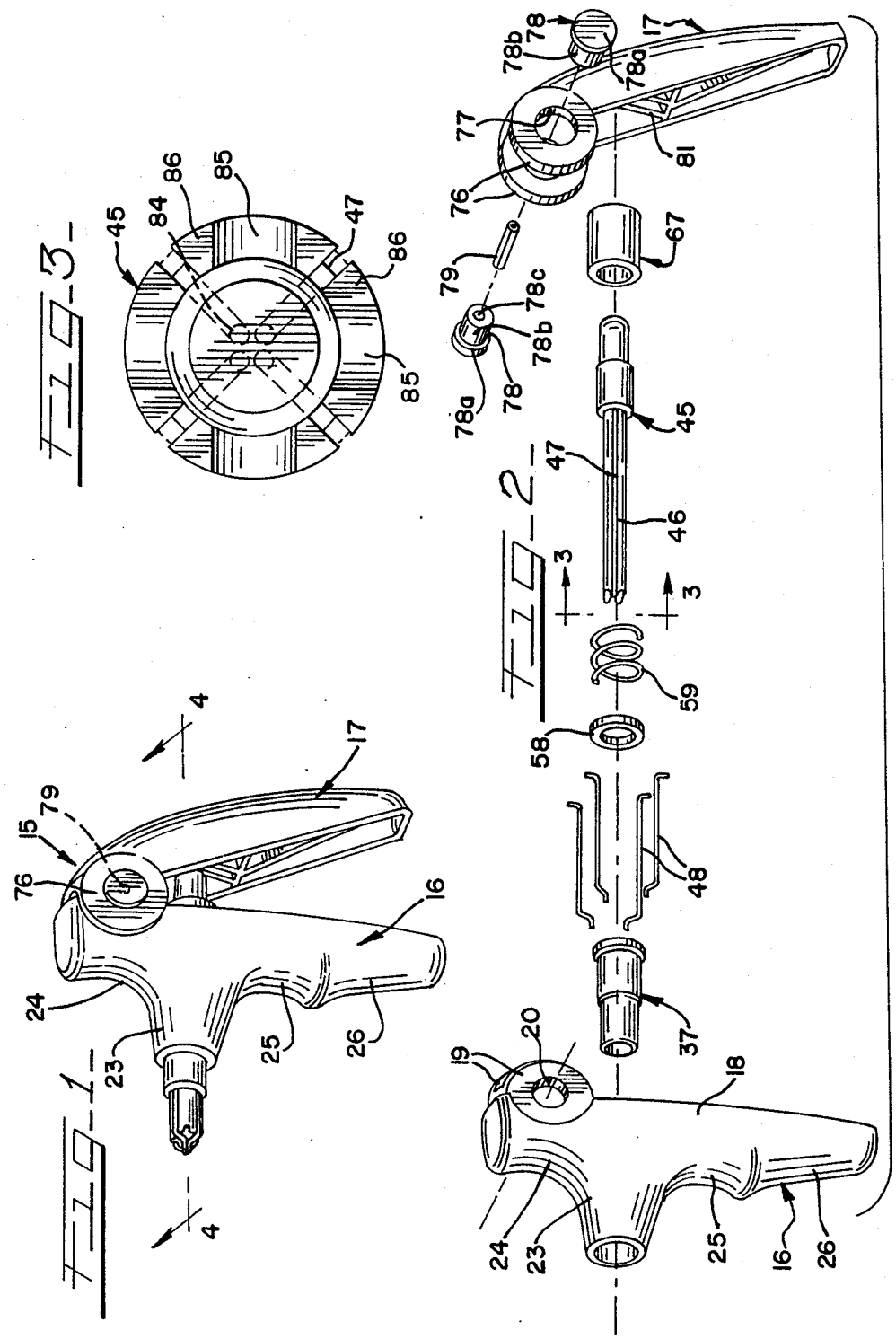

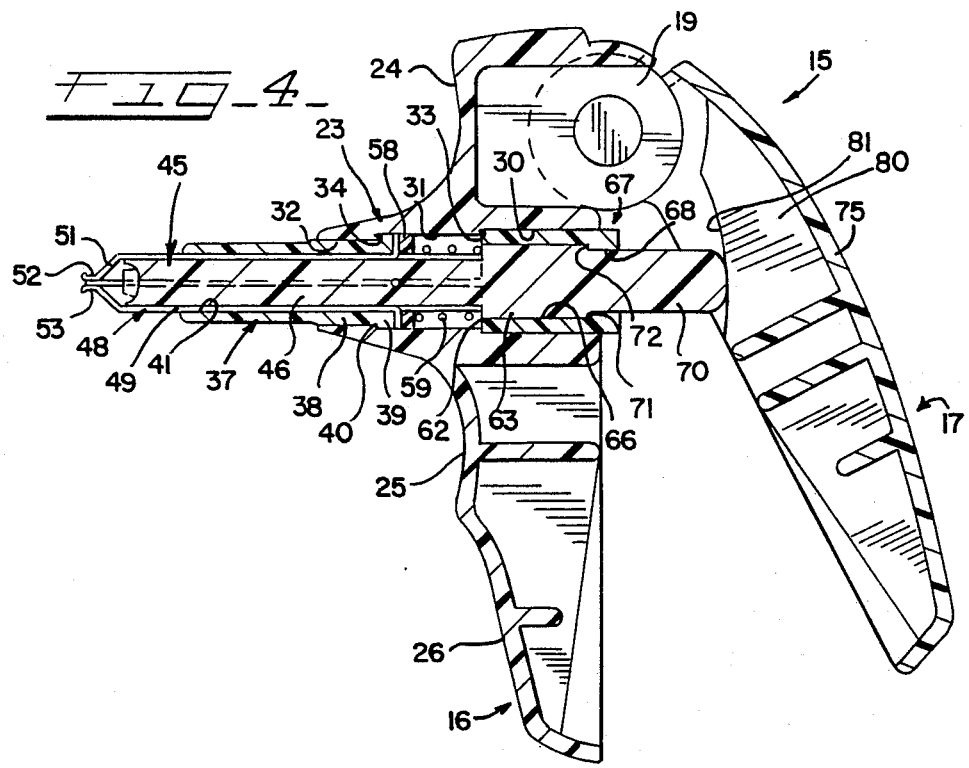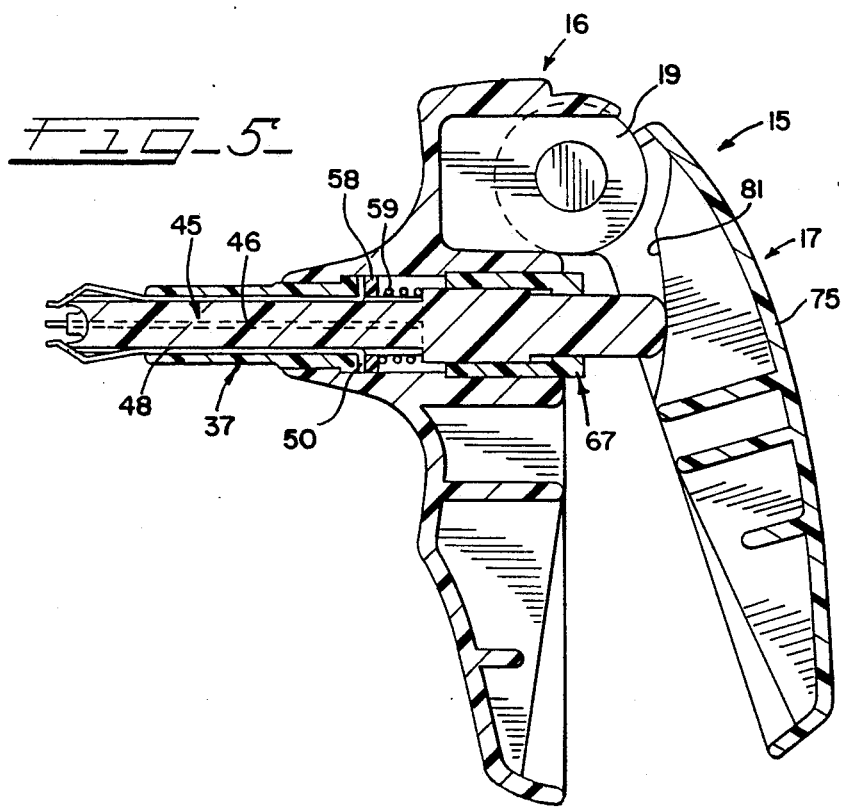

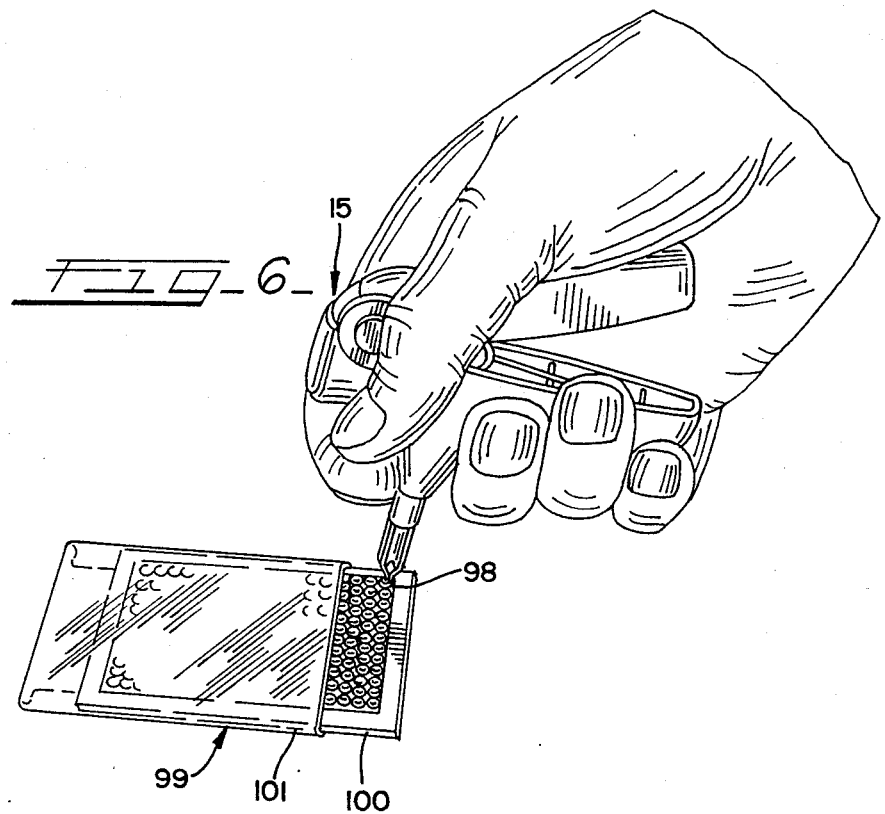
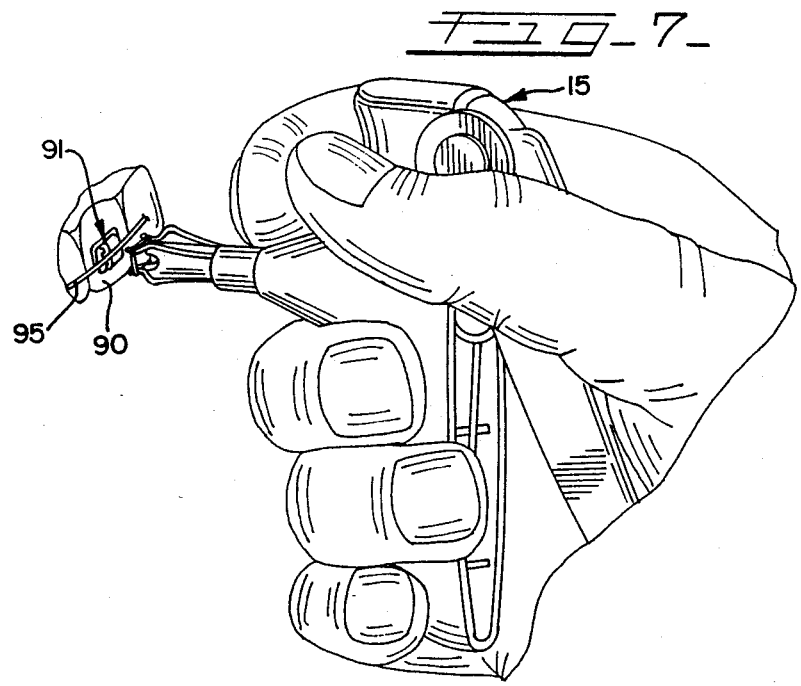

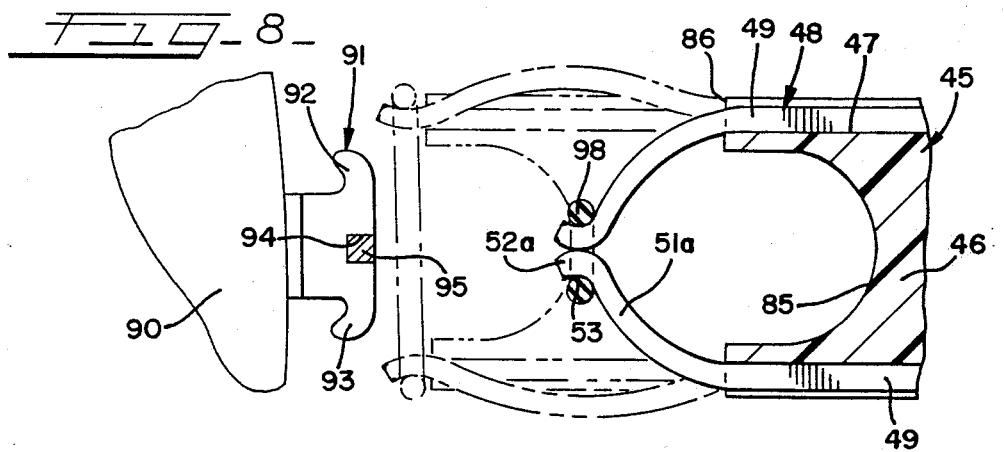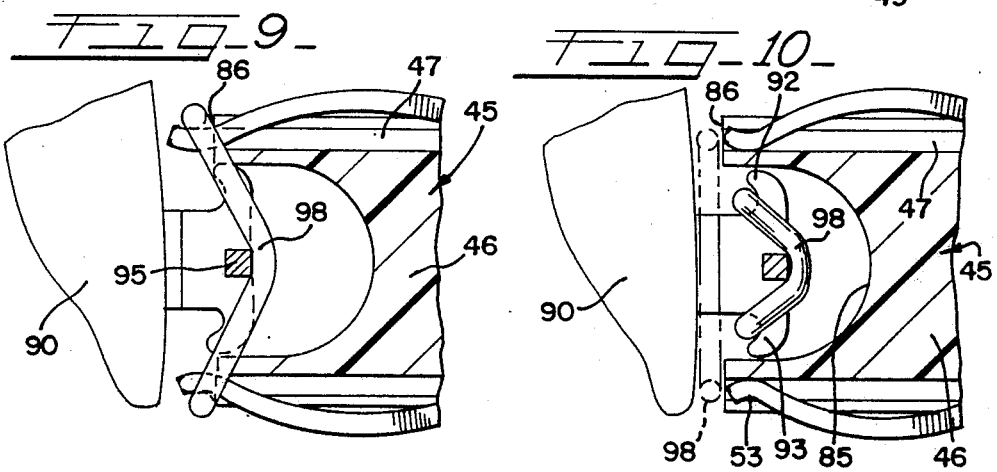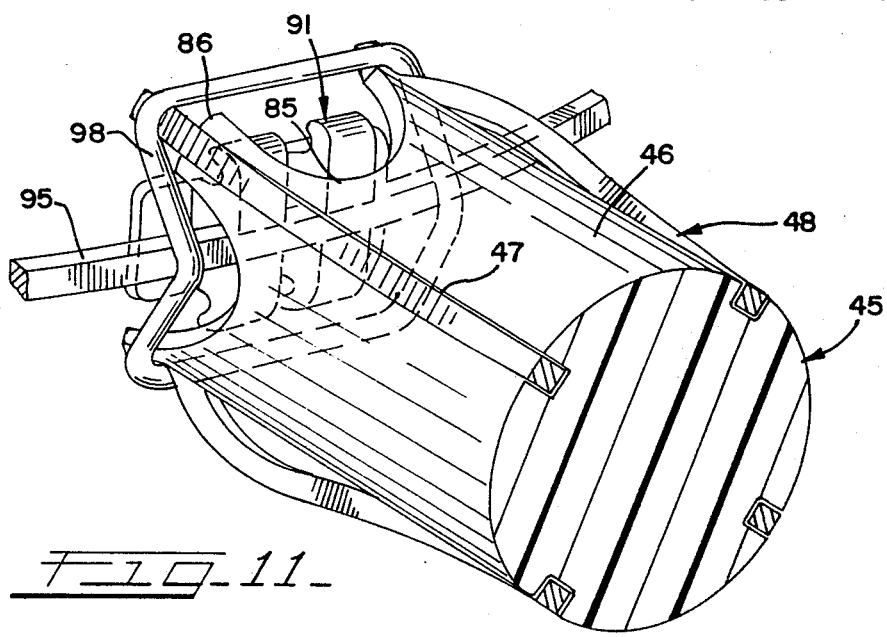

ORTHODONTIC LIGATURE GUN

DESCRIPTION

This invention relates in general to an apparatus for applying elastic ligatures to an orthodontic system, and more particularly to a ligature gun for facilitating the picking up of an elastic ligature and directly applying that ligature to an orthodontic bracket for connecting an archwire to the bracket, and still more particularly to a new and improved ligature applicator that is hand-held and which can be easily manipulated in order to reduce the time for applying ligatures onto an orthodontic system.

BACKGROUND OF THE INVENTION

Heretofore, there have been many types of devices developed and used for applying elastic ligatures to an orthodontic system and for particularly applying the ligatures directly onto an orthodontic bracket when using the ligatures for connecting an archwire to the bracket. These devices have taken many forms including the well known hemostat which takes an unstretched ligature and utilizes a bracket tie wing tip for anchoring one part of the ligature while stretching the ligature to apply it around a bracket. Another form is a pliers-like instrument having a pair of jaws that enter into the hole of the ligature and then expand to stretch the ligature before applying it to a bracket, which still requires further stretching by anchoring a part of the ligature to a tie wing tip. A still further form includes a mandrel over which a ligature is stretched and then dispensed directly from the mandrel around and onto a bracket, which requires forcing the ligature along the tapered mandrel to stretch it for application to the bracket. A still further type of applicator is in the form of an elongated handle having a wire end formed with an offset over which an elastic is stretched and then thereafter manipulated to apply the ligature to a bracket, which also requires hooking the ligature on a tie wing tip so it can be further stretched to fit around the bracket.

Each of the prior known devices has required considerable adeptness for use and has also required considerable time in order to accomplish the picking up of a ligature by the device and applying it to a bracket. Some of the devices have also sacrificed hygienic conditions.

Other problems with heretofore known applicators are their complexity of construction, difficulty to manipulate between the source of elastomeric ligatures, and/or awkward final application around the bracket itself.

SUMMARY OF THE INVENTION

The ligature gun of the present invention enables an orthodontist to reduce the time needed for applying ligatures to an orthodontic system while maintaining the integrity of hygienic conditions. It is well known that orthodontists regularly use instruments of the pliers type where coacting handles are squeezed by the hand in order to manipulate jaws or beaks to handle orthodontic wire, brackets and other accessories, making them adept at using such instruments. Accordingly, the present invention includes a hand-held device having a somewhat pistol-like grip, giving it the appearance of a gun, wherein squeezing of the handle members will cause the stretching of an elastic ligature to facilitate the direct application onto an orthodontic bracket of an orthodontic system for securing an archwire to the bracket. While the device as illustrated includes handles arranged to form a pistol-like grip, it may take other forms, as will be explained below.

The applicator of the present invention includes two members movably coacting together and operable to apply an elastomeric ligature to a bracket. The two members may be squeezable handles, hypodermic-type plunger and barrel members, or other suitably structured coacting members. A plunger is slidably guided in a supporting member and coacts with wire members having jaws formed in one position to be capable of entering into the hole of an elastic ligature, and with slight or no actuation of the plunger to grip an elastomeric ligature and remove it from a dispenser, and thereafter in a further position in order to stretch the ligature a predetermined amount so that it will easily go over the entire front profile of a bracket and be positioned for direct application around the tie wing tips of the bracket. Upon further squeezing of the handles or movement of the plunger relative to the supporting member, the plunger functions to displace the elastic ligature from the jaws of the wire members so that it will snap directly into place around the bracket behind the tie wing tips and thereafter function to properly anchor the archwire to the bracket. So, from the time that the ligature gun picks up an elastic ligature and until it is directly applied to a bracket, the hygienic condition of the ligature is maintained and the ligature need not be engaged by the hands of the orthodontist. Repeated loading of the ligature gun with ligatures and the expanding and then unloading of the ligature onto a bracket can be accomplished very quickly.

While the ligature gun of the invention in its preferred form for use in applying elastic ligatures includes a structure achieving the four-point spread of the elastic ligatures, it should be appreciated that two or more wire members may be used for expanding the ligatures within the scope of the present invention. Additionally, the applicating end of the ligature gun is structured so that it can function to carry and guide the archwire to the bracket during the application of ligatures onto the bracket.

It is therefore an object of the present invention to provide a new and improved elastic ligature applicator for applying ligatures to an orthodontic bracket quickly and positively under the best possible hygienic conditions.

Another object of the present invention is in the provision of an applicator for picking up elastic ligatures and applying them directly to an orthodontic bracket for securing the archwire to the bracket and which includes a pistol-like hand-holdable body with jaw members expandable to produce a four-point spread of an elastic ligature during application of the ligature to an orthodontic bracket.

Another object of the present invention is in providing a ligature gun for applying elastic ring or otherwise shaped ligatures to orthodontic brackets which can be inexpensively made and which greatly facilitates the application of ligatures as well as the hygienic transfer of a ligature from a ligature dispenser directly to a bracket.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of the ligature gun according to the present invention;

FIG. 2 is an exploded perspective view of the ligature gun;

FIG. 3 is an end elevational view of the plunger for the gun and looking in the direction of the arrows 3—3 of FIG. 2 and showing the wire members in phantom;

FIG. 4 is a longitudinal vertical sectional view taken substantially through the center of the ligature gun showing the parts in their home position when the handles are apart and the jaws are together and in position to enter the opening in a ligature;

FIG. 5 is a view similar to FIG. 4 but illustrating the parts when the handles are slightly compressed and where the plunger has moved to at least partially expand the jaws of the gun;

FIG. 6 is a perspective view of a person's hand with the ligature gun and illustrating the manner in which the gun fits in the hand and also the manner in which the gun is manipulated in order to engage and load a ligature on the jaws from a ligature dispenser;

FIG. 7 is a perspective view showing the gun in the hand of a person and actuated to expand the ligature in preparation for mounting the ligature onto a bracket mounted on a tooth;

FIGS. 8 to 11 show the dispensing end of the gun to illustrate its operation and also to show modified wire members where sharp bends are eliminated and the bends are arcuately formed;

FIG. 8 is a greatly enlarged view of a fragmentary tooth having an orthodontic bracket mounted onto the tooth and showing the bracket in end elevation and also illustrating the operation of the gun where in solid lines the jaw ends are shown closed with a ligature loaded on the jaws and in phantom with the ligature in expanded position in preparation for discharging the ligature around and onto the bracket;

FIG. 9 is a sequential view to FIG. 8 and showing the jaw end of the gun functioning to move the ligature over the bracket tie wing tips and archwire prior to release of the ligature;

FIG. 10 is a further sequential view showing the ligature just released in phantom and in retaining position in solid behind the tie wing tips of the bracket to lock the archwire to the bracket; and FIG. 11 is a greatly enlarged perspective view taken from the side and behind the jaw end of the gun to illustrate the manner of applying the ligature where the ligature is moved into position over the tie wing tips of the bracket and also in holding the position of the archwire in the bracket's archwire slot.

DESCRIPTION OF THE INVENTION

The ligature gun of the invention functions to permit the user to quickly apply a ligature to an orthodontic system, and more particularly to quickly apply a ligature to a bracket for connecting an archwire to the bracket and holding the archwire in the archwire slot by applying a resilient force to the archwire. The ligature is in the form of a ring or otherwise shaped continuous elastic member, like a small rubber band, and stretchable to fit behind the tie wing tips of an orthodontic bracket and lock an archwire in the archwire slot of the bracket. As it may be appreciated, the size of the ligature is quite small, as it must be capable of going over the tie wing tips of a very small orthodontic bracket mounted on a tooth and contracting to a mounted position under tension behind the tips. The ligature may be molded of any suitable natural or synthetic elastic material, or it may be formed by cutting slices along a tubular elastic material to form the ring-shaped member. While the ligature illustrated and generally used is ring-shaped, it may be otherwise shaped as long as it is a continuous strand with a hole. The type of elastic ligatures that are susceptible to being applied to a bracket by the ligature gun of the invention have been well known and heretofore have been applied to an orthodontic bracket of an orthodontic system by use of many types of tools and techniques. Preferably, the ligatures to be applied by the ligature gun of the invention are molded and have a substantially round cross section through one-half of the ligature, and preferably they are individually provided in a dispenser, although it will be appreciated that the gun of the present invention could also function to engage and remove a ligature that has been molded to a support member in a fashion that it can be easily separated from the support member with a nominal force.

The ligature gun of the invention, when used, will first function to engage a ligature which constitutes loading the ligature gun with a ligature. Thereafter, the ligature gun can be operated to first expand the ligature so as to permit it to be telescopically mounted on a bracket and thereafter to release or shoot the ligature from the gun where it will contract and catch on the tie wings of a bracket and lock an archwire in place on the bracket. The gun is also structured so that it can assist in guiding the archwire to the archwire slot of the bracket and then inserting the archwire into that slot prior to release of the ligature for securing the archwire to the bracket. Operation of the ligature gun is accomplished by the hand of a person gripping the handles and merely by first inserting the jaw ends of the gun into a ligature and removing it from a dispenser and, secondly, to squeeze the handles to expand the ligature so that it can go over the tie wing tips of a bracket, and finally to squeeze the handles further to eject the ligature from the gun. These steps can be very quickly taken as the ligature dispenser would be normally held in one hand of the user, the gun in the other hand, and moving from the dispenser to the mouth of a patient and aligning with a bracket would be accomplished in a very short time. Further, this would enable the user to achieve greater hygienic transfer of a ligature from a dispenser to the mouth of a patient than has heretofore been possible.

The ligature gun of the invention in its broadest form includes a first member and a second member movable relative to the first member. One of the members is a support for the other member that may be in the form of a plunger operable to manipulate at least a pair of wire-like members to grip and expand a ligature and then discharge the ligature around a bracket.

Referring now to the drawings, and particularly to FIGS. 1 to 5, the ligature gun of the invention, generally indicated by the numeral 15, includes a pistol-shaped body having a first finger-engaging member or handle 16 and a second palm-engaging member or handle 17 that is pivotally connected to the first member 16 for gripping and operating the gun. The first member 16 further includes an upright elongated body 18 having a pair of ears 19 at the upper end provided with centrally positioned and aligned openings 20 serving as bearing member for the palm-engaging member 17. As seen particularly in FIGS. 4 and 5, the first finger-engaging member or handle 16 is hollowed to reduce its weight and provided with reinforcing ribs for strengthening the member. Spaced slightly down from the top end of the first finger-engaging member and immediately below the ears 19, is a forwardly projecting necked portion 23. Just above the necked portion 23 is one finger-engaging surface or area 24, while below the necked portion finger-engaging surfaces or areas 25 and 26 are arranged in alignment with each other. When handling the ligature gun, the index finger is usually positioned along the surface 24, while the other three fingers are positioned along the surfaces 25 and 26.

As seen particularly in FIGS. 4 and 5, a stepped bore extends through the first finger-engaging member and the necked portion 23 and which includes successively smaller bores 30, 31 and 32 defining internal shoulders 33 and 34. These bores are cylindrical in shape, although it may be appreciated that they may be otherwise configured so long as the parts fitting in the bores are matingly configured. Within the smallest bore 32 a barrel or tubular member 37 is positioned and which includes an outer diametrical portion 38 that matingly fits in the bore 32 and a second outer diametrical portion 39 that matingly fits within the bore 31. Between the diametrical portions 38 and 39, a shoulder 40 is defined which abuts against the shoulder 34 of the stepped bore, thereby positioning the barrel 37 at a given location within the stepped bore. The barrel further includes a cylindrical guide bore 41 which slidably receives a mating cylindrical plunger 45. As previously mentioned, the barrel may be polygonally or otherwise cross-sectionally shaped, and then the plunger would also be polygonally or otherwise cross-sectionally shaped to mate with the barrel.

The plunger 45 includes at one end a cylindrically formed portion 46 matingly received by the guide bore 41 of the barrel 37 and sized so that it will easily slide in the guide bore. A plurality of circumferentially spaced and longitudinally extending slots or grooves 47, peripherally of the plunger, are adapted to receive wire or wirelike members 48. The wirelike members may preferably be of a spring steel, but may be of plastic, fiberglass or other suitable material. So, the words "wire" or "wirelike" are intended to cover members of a suitable springy material.

Each member includes an intermediate portion 49 that is disposed in a groove but in slidable relation thereto, and an anchoring end portion 50 formed by a leg that is bent at substantially right angles to the intermediate portion 49 and which serves to anchor the wire members at a given position relative to the first finger-engaging member 16. At the jaw end of one form of each wire member, as seen in FIGS. 1 to 7, a leg 51 extends at an obtuse angle to the intermediate portion 49 and a leg 52 bent at an obtuse angle to the leg 51 coact to define a jaw 53 for gripping engagement with a ligature. Optionally, the relatively sharp bends may be arcuately formed as seen in FIGS. 8 to 11, where an arcuate segment 51a extends downwardly from the intermediate portion 49 and terminates in a reversely bent arcuate segment 52a to define jaw 53. This embodiment eliminates the relatively sharp bends in the previous embodiment. The tip ends of the wire members are preferably smooth and rounded to facilitate engagement with a ligature, as the jaws go to a desired engaging position. So, each of the wire members includes a jaw 53 which is at the forward terminal ends of the wire members and which coact with each other to engage and expand a ligature when the gun is actuated. The barrel 37 retains the wire members 48 in the plunger grooves. The length of the wire members is such that when in the home position the first portion 51 or 51a bends from the intermediate portion 49 substantially at the free end of the plunger 46.

Although the ligature gun illustrated shows the use of four wire members, it should be appreciated that the gun could include two or more wire members. Where only two members would be provided, it would then not be possible to open the ligature entirely, but it would merely be possible to stretch it.

While the wire members are positioned in grooves or slots on the outside of the plunger, it can be appreciated that the grooves or slots could be formed on the inside of the barrel 37 and held in place by the plunger or formed partly on each of the plunger and the barrel.

The anchoring ends 50 of the wire members are held in place against the inner end of the barrel 37 by a washer 58 which is in turn received within the bore 31 and resiliently biased against the wires by a helical spring 59 that encircles the forward plunger portion 46. The other end of the spring bottoms on an annular shoulder 62 formed on the plunger by a cylindrically enlarged portion 63 which is slidably received within a bore 66 of a retainer bushing 67. The retainer bushing 67 also includes a stepped down bore 68 which slidably receives a reduced cylindrical portion 70 of the plunger. The reduced portion 70 forms an annular stop shoulder 71 which coacts to engage the annular shoulder 72 formed between the bores 66 and 68 of the retainer bushing 67. The spring 59 is structured and sized to drive the plunger to its home position so that the stop 71 engages the bushing stop 72. While the retainer bushing 67 may be secured in any desired way in the bore 30 of the first finger-engaging portion, it will be appreciated that it may be press-fit therein to lock it in place with the finger-engaging member.

The second palm-engaging member 17 which is pivotally mounted on the first finger-engaging member 16 is in the form of an elongated member 75 of substantially equal length to the first finger-engaging member so as to complement the first member when the ligature gun is held in the hand of a person. As particularly seen in FIGS. 6 and 7, the second palm-engaging member 17 fits in the palm of a person's hand so that pressure can be applied to actuate the plunger 45. The palm-engaging side of the member 17 is rounded and smooth for comfort to the hand. At the upper end of the member 17, a pair of ears 76 in parallel spaced relation and having centrally disposed openings 77 coact with the ears 19 as the member 17 is mounted on the member 16. A handle pin comprised of a pair of identical pin members 78 held together by a roll pin 79 are fitted in the openings 77 and 20 in order to pivotally mount the handle 17 to the member 16. Both pin members include head sections 78a that are bearingly received in openings 77 and reduced sections 78b that are bearingly received in openings 20 of ears 19. Central bores 78c receive a roll pin 79 in press-fit relation to hold pin members 78 in place. As seen particularly in FIGS. 1 and 2, the ears 76 of the handle 17 overlap the ears 19 of the first member 16 and openings 77 of ears 76 are larger than openings 20 of ears 19.

The handle 17 includes on its interior a cam 80 having a cam surface 81 engaging the rounded rear or back end of the plunger 46, whereby upon pivotal movement of the handle 17 relative to the first member 16 will cause the riding of the rear or back end of the plunger against the cam surface 81 and the movement of the plunger to actuate the gun.

The front end of the plunger 46, as seen particularly in FIGS. 3 and 8 to 10, includes a recessed area or hollow 84 that is sized to be larger than the labial or front profile of the bracket onto which a ligature is to be mounted as it is necessary to advance the discharge end of the plunger over the bracket, as seen particularly in FIGS. 9 to 11, at the time the ligature is shot from the gun, so that the ligature is behind the tie wing tips.

At the front end of the plunger and preferably in equally circumferential spacing, four cutouts 85 are provided to accommodate the archwire when the plunger end is moved over the bracket to discharge the ligature. Thus, two pairs of cutouts will be diametrically opposed to each other which then permit orientation of the gun either vertically, as illustrated in FIG. 7, or horizontally when applying a ligature to a bracket. As seen particularly in FIGS. 9 to 11, the cutouts or notches 85 allow the head end of the plunger to be advanced toward the tooth and in complete overlying relation to the bracket and the archwire.

The cutouts define terminal ends or nose portions 86 that are aligned with the longitudinal slots or grooves 47 along which the wire members 48 extend. Thus, the slots 47 open through the terminal ends 86 of the plunger and, as will be more clearly explained, serve to dislodge or discharge the ligature from the jaws of the wire members upon obtaining sufficient movement of the plunger 46 relative to the barrel.

In operation, a ligature is first loaded onto the jaws of the ligature gun and transferred to the mouth of a patient and then discharged onto a bracket to lock an archwire in place. For purposes of further explaining the operation, reference is made particularly to FIGS. 6 to 11. A front perspective view of a portion of the arch is illustrated in FIG. 7 with a tooth 90 having a typically constructed edgewise bracket 91 mounted on the tooth. The tooth 90 and bracket 91 are shown in end profile in FIGS. 8 to 10, and the bracket 91 is shown by itself in FIG. 11 for clarity. The bracket 91 includes upper and lower tie wing tips 92 and 93 and an archwire slot 94 that is horizontally opening and which is configured to receive a rectangular archwire 95.

A ligature 98 is first loaded onto the gun, and, as illustrated in FIG. 6, a ligature dispenser, the structure of which is more particularly disclosed in a copending application owned by the assignee of this application, is preferably used for loading ligatures on the gun. For the explanation of the operation of the ligature gun, dispenser 99 includes a tray 100 in which the ligatures are contained and held in place by a releasable adhesive. A cover member 101 slidably carried on the tray 100 is slid to an open position so that ligatures are exposed. The ligatures are sized so that they will fit on the jaws of the gun, as seen in FIG. 8, so that it then can be transferred to an orthodontic system. Thereafter, the ligature gun is brought to the mouth of a patient and pressure is applied to drive the plunger to cam the jaw ends of the wire members and expand the ligature, as shown in phantom in FIG. 8, and in solid lines in FIGS. 7, 9 and 11. The expansion is continued until it will stretch the ligature so that it can be directly applied over the face of the bracket. At this point, the nose ends 86 of the plunger are positioned just short of the jaws 53, as seen in phantom in FIG. 8. Alignment of the end of the ligature gun plunger with the bracket will allow the ligature then to go over the labial face of the bracket to a position behind the wing tips, as seen in FIGS. 9 and 11, where it can then be discharged or shot onto the bracket. At this point, additional pressure will be applied to the handle 17 to advance the plunger so that the nose ends 86 will engage the ligature 98 and push the ligature off the jaws of the wire members where it can be seen in phantom in FIG. 10 in suspension prior to snapping into place on the bracket to secure the archwire 95 to the bracket, as seen in FIG. 10.

As seen in FIGS. 9 and 11, the ligature 98, when engaging the archwire 95, by virtue of being expanded on the jaws of the gun, can be guided into position in the archwire slot. Thus, the gun can assist in lifting and placing the archwire in the bracket if it is not already in place. The notches or cutouts 85 function to allow the discharge end of the plunger to move over the bracket, while not engaging or bending the archwire and where the ligature serves to hold the archwire in place before it is discharged from the gun into securing position. As seen particularly in FIG. 10, the ligature ultimately mounted on the bracket catches behind the tie wing tips 92 and 93 and engages over the labial face of the archwire to hold the archwire in place.

The four wire members on the plunger provide a four-point spread of the elastic ligature to facilitate the mounting of a ligature on a bracket. Thus, it will be appreciated by manipulation of the gun by the hand a ligature may be easily mounted, transferred to the mouth of a patient, expanded and then discharged around a bracket.

It will be understood that the size of the gun parts may vary depending upon the size of the ligatures to be handled and the size of the brackets onto which the ligatures are to be mounted. While not shown, it will be appreciated that the plunger may be constructed to be adjustable lengthwise for adjusting the stroke of the plunger and the coaction with the wire jaws. Further, it may be understood that a ratchet mechanism may be built into the gun which would operate like such a mechanism used with hemostats where the plunger could be ratcheted from one position to another to further facilitate the loading, partial expansion and release of a ligature. Except for the wire members if made of metal, the spring, and the roll pin, the gun is generally made of a suitable plastic.

It will be understood that modifications and variations may be effected without departing from the scope of the novel concepts of the present invention, but it is understood that this application is to be limited only by the scope of the appended claims.

The invention is hereby claimed as follows:

1. A device for applying elastic ligatures to an orthodontic bracket, said device having a first member with an elongated guide bore, a plunger slidably mounted in the bore, at least two longitudinally extending flexible wire members guidably retained by the plunger and guide bore, each having an intermediate portion extending along the plunger and guide bore and one end anchored to said first member, and the other end disposed beyond the free end of the plunger and formed to coact with the like end of the other wire member so that the two ends form jaws that can enter into an opening in an elastic ligature when in substantial abutting relation with each other, and a second member for actuating the plunger wherein the plunger when slidably actuated separates the jaws for expanding a ligature received thereon and thereafter pushes or discharges the ligature from the free ends of the jaws, whereby the device will function to first engage and grip an elastic ligature and thereafter expand the ligature for application to an orthodontic system and then push or shoot the ligature from the jaws and around the bracket.

2. The device of claim 1, wherein the intermediate portion of each wire member is straight and the anchored end is bent at substantially right angles to engage said first member.

3. The device of claim 2, wherein the jaw of each wire member includes a first leg bent at an obtuse angle to the intermediate portion and a second leg bent at an obtuse angle to the first leg to define with said first leg a ligature gripping jaw, whereby the free end of the plunger functions to cam the first legs to spread the jaws during advancing the plunger along the wire members.

4. The device of claim 1, wherein the second member is pivotally mounted on the first member.

5. The device of claim 1, wherein a return spring is mounted in said first member for biasing the plunger and second member to home position where the jaws are closed and ready for engagement in another ligature.

6. The device of claim 1, which includes four flexible wire members equally circumferentially spaced about said plunger to define a four-point spread of a ligature stretched for application to a bracket.

7. The device of claim 6, wherein pusher portions are defined at the free end of the plunger in alignment with the wire members to discharge the ligature from the jaws.

8. The device of claim 7, wherein notches or cutouts are formed at the free end of the plunger between the pusher portions to accommodate the archwire during application of a ligature around a bracket.

9. A ligature gun for applying elastic ligatures to an orthodontic bracket having an archwire in an archwire slot to secure the archwire to the bracket, said gun comprising a finger-engaging member and a palm-engaging member movably mounted on the finger-engaging member, a barrel fixedly carried by said finger-engaging member, a plunger slidably received in said barrel and having a front ligature discharge end extending from the front end of the barrel and a rear driving end extending from the rear end of the barrel, stop means in said finger-engaging member for limiting the rearward movement of the plunger and defining a home position relative to said finger-engaging member, spring means biasing said plunger to said home position, means on said palm-engaging member drivingly engaging the plunger to cause sliding of said plunger in said barrel, longitudinally extending flexible wirelike members, said barrel and plunger having means for guidably retaining said wirelike members, means anchoring the rear ends of the wirelike members to said finger-engaging member, the outer ends of the wirelike members extending beyond the discharge end of the plunger and being formed to define ligature jaws and jaw spreading portions, whereby extension of the plunger through the barrel causes the discharge end to first spread the jaws and a ligature carried by the jaws and then discharge the ligature from the jaws.

10. The ligature gun of claim 9, wherein the wirelike members are equally spaced apart on the plunger.

11. The ligature gun of claim 9, wherein said means for guidably retaining said wirelike members include grooves along the periphery of said plunger closed by said barrel.

12. The ligature gun of claim 11, wherein the front ligature discharge end of the plunger is notched between the grooves to accommodate the archwire when placing a ligature on a bracket.

13. The ligature gun of claim 12, wherein each notch is diametrically opposite another notch.

14. The ligature gun of claim 13, wherein said plunger further includes pusher portions disposed between adjacent notches that serve to push or discharge a ligature from the jaws upon extension of the plunger toward the jaw ends of the wire members.

15. The ligature gun of claim 14, wherein the wirelike members include a straight section received in a plunger groove, and a first leg bent at an obtuse angle to the straight section and a second leg bent at an obtuse angle to the first leg to define therewith a ligature gripping jaw, whereby the free end of the plunger functions to cam the first legs to spread the jaws during advancing the plunger along the wirelike members.

16. The ligature gun of claim 14, wherein the wirelike members include a straight section received in a plunger groove, a first arcuate segment extending from the straight section and toward a center line extending through said plunger, and a second arcuate segment extending from the first arcuate segment and reversely bent to define therewith a ligature gripping jaw, whereby the free end of the plunger functions to cam the first arcuate segments to spread the jaws during advancing the plunger along the wirelike members.

17. The ligature gun of claim 15 or 16, wherein the anchored ends of the wirelike members include a leg bent at substantially right angles to the straight section.

18. The ligature gun of claim 17, wherein the plunger grooves are rectangular in cross section and said wirelike members are rectangular in cross section.

* * * * *